United States Patent [19]
Campbell et al.

[11] Patent Number: 4,616,024
[45] Date of Patent: Oct. 7, 1986

[54] DIHYDROPYRIDINE ANTI-ISCHAEMIC AND ANTIHYPERTENSIVE AGENTS

[75] Inventors: Simon F. Campbell, Deal; Peter E. Cross, Canterbury; John K. Stubbs, Deal, all of England

[73] Assignee: Pfizer Inc., New York, N.Y.

[21] Appl. No.: 704,103

[22] Filed: Feb. 21, 1985

Related U.S. Application Data

[60] Division of Ser. No. 515,231, Jul. 19, 1983, Pat. No. 4,515,799, and a continuation-in-part of Ser. No. 463,095, Feb. 2, 1983, abandoned.

[30] Foreign Application Priority Data

Jul. 22, 1982 [GB] United Kingdom ............... 8221214

[51] Int. Cl.⁴ .................... C07D 401/12; A61K 31/41
[52] U.S. Cl. .................... 514/340; 546/276; 546/269; 546/257; 546/284; 546/281; 546/280; 546/277; 514/314; 514/337; 514/338; 514/339; 514/342; 514/343
[58] Field of Search ............... 546/276, 269, 274, 257, 546/167, 270, 271, 284, 256, 281, 280, 277; 514/337, 338, 339, 340, 341, 342, 343, 314

[56] References Cited

U.S. PATENT DOCUMENTS

| | | | |
|---|---|---|---|
| 3,905,983 | 9/1975 | Bossert et al. | 546/321 |
| 3,943,140 | 3/1976 | Bossert et al. | 546/329 |
| 3,946,027 | 3/1976 | Bossert et al. | 546/257 |
| 3,946,028 | 3/1976 | Bossert et al. | 546/257 |
| 4,177,278 | 12/1979 | Bossert et al. | 514/356 |
| 4,188,395 | 2/1980 | Bossert et al. | 514/333 |
| 4,404,378 | 9/1983 | Miyano et al. | 546/281 |
| 4,430,332 | 2/1984 | Campbell et al. | 546/284 |
| 4,430,333 | 2/1984 | Campbell et al. | 546/281 |
| 4,532,248 | 7/1985 | Franckowiak et al. | 514/345 |

FOREIGN PATENT DOCUMENTS

| | | |
|---|---|---|
| 0031801 | 7/1981 | European Pat. Off. |
| 0100189 | 2/1984 | European Pat. Off. |
| 55-47656 | 4/1980 | Japan |
| 1552911 | 9/1979 | United Kingdom |
| 2034693 | 6/1980 | United Kingdom |
| 1585978 | 3/1981 | United Kingdom |

OTHER PUBLICATIONS

Bossert et al., Angew. Chem. Int. Ed. Engl. 20, 762–769, 1981.

*Primary Examiner*—Jane T. Fan
*Attorney, Agent, or Firm*—Charles J. Knuth; Albert E. Frost; James M. McManus

[57] ABSTRACT

1,4-Dihydropyridine derivatives of the formula:

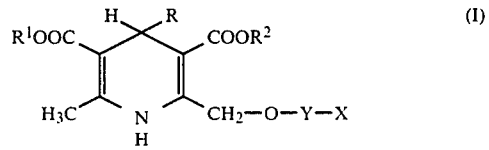

wherein R is aryl or heteroaryl: $R^1$ and $R^2$ are each independently $C_1$–$C_4$ alkyl or 2-methoxyethyl; Y is $-(CH_2)_n-$, $-CH_2CH(CH_3)-$ or $-CH_2C(CH_3)_2-$; n is 1 to 3; and X is a 5 or 6 membered nitrogen containing aromatic heterocyclic ring which may optionally be substituted by one or more $C_1$–$C_4$ alkyl, phenyl, benzyl, CN, $-N(R^3)_2$, $(CH_2)_mCO_2H$, $(CH_2)_mCO_2(C_1$–$C_4$ alkyl) or $(CH_2)_mCON(R^3)_2$ group wherein each $R^3$ is independently H or $C_1$–$C_4$ alkyl and m is 0 or 1; and their pharmaceutically acceptable acid addition salts, and pharmaceutical preparation containing such compounds, have utility as anti-ischaemic and antihypertensive agents.

6 Claims, No Drawings

DIHYDROPYRIDINE ANTI-ISCHAEMIC AND ANTIHYPERTENSIVE AGENTS

This application is a division of U.S. patent application Ser. No. 515,231, filed July 19, 1983, now U.S. Pat. No. 4,515,799, issued May 5, 1985 which in turn is a continuation-in-part of copending U.S. patent application Ser. No. 463,095, filed Feb. 2, 1983 now abandoned.

BACKGROUND OF THE INVENTION

This invention relates to certain dihydropyridines, specifically to certain 1,4-dihydropyridines having an aromatic heterocyclic group in a side chain attached to the 2-position, which have utility as anti-ischaemic and antihypertensive agents, and to pharmaceutical preparations containing such compounds.

The compounds of the invention reduce the movement of calcium into the cell and they are thus able to delay or prevent the cardiac contracture which is believed to be caused by an accumulation of intracellular calcium under ischaemic conditions. Excessive calcium influx during ischaemia can have a number of additional adverse effects which would further compromise the ischaemic myocardium. These include less efficient use of oxygen for ATP production, activation of mitochondrial fatty acid oxidation and possibly, promotion of cell necrosis. Thus the compounds are useful in the treatment or prevention of a variety of cardiac conditions, such as angina pectoris, cardiac arrythmias, heart attacks and cardiac hypertrophy. The compounds also have vasodilator activity since they can inhibit calcium influx in cells of vascular tissue and they are thus also useful as antihypertensive agents and for the treatment of coronary vasospasm.

SUMMARY OF THE INVENTION

According to the invention, there are provided novel 1,4-dihydropyridine derivatives of the formula:

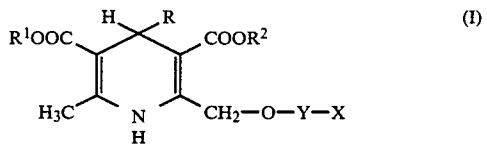

or their pharmaceutically acceptable acid addition salts, wherein:

R is aryl or heteroaryl;

$R^1$ and $R^2$ are each independently $C_1$-$C_4$ alkyl or 2-methoxyethyl;

Y is $-(CH_2)_n-$, $-CH_2CH(CH_3)-$ or $-CH_2C(CH_3)_2-$;

n is 1 to 3; and

X is 5 or 6 membered nitrogen containing aromatic heterocyclic ring which may be substituted by one or more $C_1$-$C_4$ alkyl, phenyl, benzyl, cyano, $-N(R^3)_2$, $(CH_2)_mCO_2H$, $(CH_2)_mCO_2(C_1$-$C_4$ alkyl) or $(CH_2)_mCON(R^3)_2$ groups wherein each $R^3$ is independently H or $C_1$-$C_4$ alkyl and m is 0 or 1; with the proviso that if the aromatic heterocyclic ring is linked to Y by a ring nitrogen atom, n is 2 or 3.

The term "aryl" as used in this specification, includes phenyl and phenyl substituted by one or two substituents selected from nitro, halo, $C_1$-$C_4$ alkyl, $C_1$-$C_4$ alkoxy, hydroxy, trifluoromethyl, and cyano. It also includes 1- and 2-naphthyl.

The term "heteroaryl" as used in this specification for R means an aromatic heterocyclic group which may optionally be substituted and includes, for example, benzofuranyl; benzothienyl; pyridyl optionally monosubstituted by methyl, thiomethyl, cyano or halo; quinolyl; benzoxazolyl; benzthiazolyl; furyl; pyrimidinyl; thiazolyl; 2,1,3-benzoxadiazol-4-yl; 2,1,3-benzthiadiazol-4-yl; and thienyl optionally monosubstituted by halo or $C_1$-$C_4$ alkyl.

The nitrogen containing aromatic heterocyclic ring X may contain as heteroatom one or more nitrogen atoms and may also contain an oxygen or sulphur atom. The ring may be linked to Y either by a ring carbon or ring nitrogen atom with the proviso that if the heterocyclic ring X is linked by a ring nitrogen atom n must be 2 or 3. Thus examples of suitable heterocyclic ring systems include pyridyl, pyrrolyl, imidazolyl, triazolyl, tetrazolyl, thiazolyl, thiadiazolyl and oxadiazolyl. The heterocyclic ring may be substituted or unsubstituted. Preferred substituents are $C_1$-$C_4$ alkyl, carbamoyl, carbamoylmethyl, amino or di($C_1$-$C_4$ alkyl)amino groups. Thus particular and preferred examples of X include 2,4,5-trimethyl-1-imidazolyl; 6-dimethylamino-3-pyridyl 1-methyl-2-imidazolyl; 1,2,3-(1H)-triazol-1-yl; 4-carbamoyl-1,2,3-(1H)-triazol-1-yl; 3-amino-1,2,4-triazol-5-yl; 5-methyl- and 5-amino-1,3,4-thiadiazol-2-yl; 5-methyl-1,3,4-oxadiazol-2-yl; 1- and 2-methyl and 1- and 2-(carbamoylmethyl)tetrazol-5-yl.

"Halo" means fluoro, chloro, bromo or iodo.

Alkyl and alkoxy groups having 3 or more carbon atoms can be straight or branched chain.

R is preferably 2-chlorophenyl or 2,3-dichlorophenyl. $R^1$ and $R^2$ are preferably $CH_3$ or $C_2H_5$, especially when $R^1$ is $CH_3$ and $R^2$ is $C_2H_5$. Y is preferably $-(CH_2)_2-$.

Particularly preferred compounds are those wherein R is 2-chlorophenyl or 2,3-dichlorophenyl, $R^1$ is $CH_3$, $R^2$ is $C_2H_5$, and X is 2,4,5-trimethyl-1-imidazolyl; 1,2,3-(1H)-triazol-1-yl; 4-carbamoyl-1,2,3-(1H)-triazol-1-yl; 5-methyl-1,3,4-thiadiazol-2-yl; 5-methyl-1,3,4-oxadiazol-2-yl; 3-amino-1,2,4-triazol-5-yl or 1- or 2-methyl or 2-(carbamoylmethyl)tetrazol-5-yl.

DETAILED DESCRIPTION OF THE INVENTION

The compounds of the formula (I) containing one or more asymmetric centres will exist as one or more pairs of enantiomers, and such pairs or individual isomers may be separable by physical methods, e.g. by fractional crystallisation of the free bases or suitable salts or chromatography of the free bases. The invention includes the separated pairs as well as mixtures thereof, as racemic mixtures or as separated d- and l- optically-active isomeric forms.

The pharmaceutically acceptable acid addition salts of the compounds of the formula (I) are those formed from acids which form non-toxic acid addition salts, for example the hydrochloride, hydrobromide, sulphate, or bisulphate, phosphate or acid phosphate, acetate, citrate, fumarate, gluconate, lactate, maleate, succinate and tartrate salts.

The compounds of the invention can be prepared by a number of different processes according to the invention.

(a) In one process the compounds of formula I can be prepared by the Hantzsch synthesis, according to the following reaction scheme:

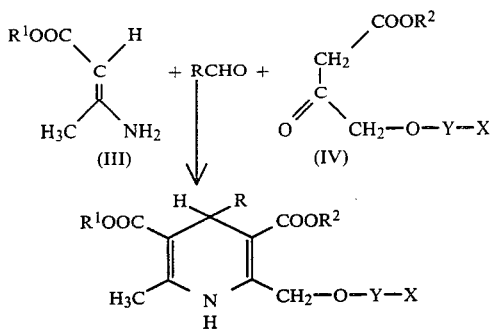

In a typical procedure, the ketoester (IV) and aldehyde are heated under reflux in a suitable organic solvent, e.g. a $C_1$–$C_4$ alkanol such as ethanol, for about 15 minutes, and then the amino-crotonate (III) is added. Alternatively the aminocrotonate (III), the ketoester (IV) and the aldehyde can be heated together in the solvent. Preferably a small amount of a lower alkanoic acid such as acetic acid is added to neutralise the solution. The resulting solution can then be heated at 60°–130° C., preferably under reflux, until the reaction is essentially complete, typically in 24 hours or less. The product of the formula (I) can then be isolated and purified by conventional procedures, for example by partition recrystallisation or by chromatography.

The ketoesters (IV) are either known compounds or can be prepared by methods analogous to those of the prior art, such as the method illustrated in the Preparation 1 hereinafter, which is essentially the method of Troostwijk and Kellogg, J. C. S. Chem. Comm., 1977, page 932. Similarly the amino-crotonates (III) are either known compounds or can be prepared by conventional procedures. Also the aldehydes are either known or can be prepared by known methods in accordance with literature precedents.

(b) In an alternative process the compounds of formula (I) can be prepared by the following process:

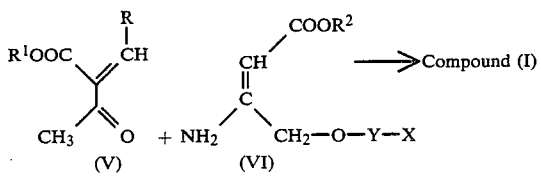

The crotonate (VI) is typically prepared in situ by reaction of the corresponding ketoester (IV):

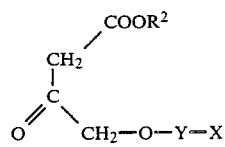

with ammonium acetate, e.g. by refluxing in a suitable organic solvent, e.g. a $C_1$–$C_4$ alkanol such as ethanol, for, up to an hour. The crotonate (VI) is then reacted with compound (V), typically by heating in the solvent for up to about 5 hours at 60°–130° C., e.g. under reflux.

The product (I) can then be isolated and purified by conventional procedures as before.

In the case of compounds of the formula I in which the heterocyclic ring is substituted by an N-benzyl group, this may be removed by a conventional catalytic hydrogenation (for example by hydrogenating at 50 p.s.i. for 16 hours in the presence of palladium on charcoal catalyst) to yield the corresponding unsubstituted compound.

The starting materials (V) are either known compounds or may be prepared by methods analogous to those of the prior art in accordance with literature precedents, see for example Can. J. Chem., 1967, 45, 1001.

It will be appreciated that while all the compounds of the invention may be prepared by the processes described under (a) or (b) above, in certain individual cases particular compounds may more conveniently be prepared starting with the preformed dihydropyridine. Such processes will vary according to the nature of the aromatic heterocyclic ring X desired. The following processes describe examples of processes for preparing the compounds of formula (I) containing particular aromatic heterocyclic rings but other alternatives and variations will be evident to those skilled in the art.

(c) Thus in a further process, compounds of the formula (I) wherein X is a 1,2,3-triazole ring may be prepared from the corresponding azide of formula:

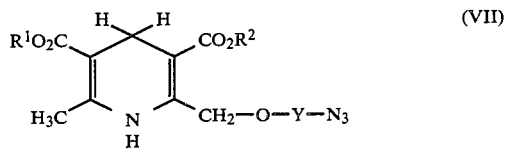

where R, $R^1$, $R^2$ and Y are as previously defined, by reacting with an acetylene e.g. a $C_1$–$C_4$ alkyl ester of acetylene dicarboxylic or propiolic acids. The reaction is performed by heating the reactants together, generally in equimolar quantities, in a reaction inert organic solvent, e.g. toluene. A period of up to 10 hours at reflux temperature may be necessary depending on the reactants and the particular solvent selected, and the desired product may then be isolated and purified in accordance with conventional procedures.

In the case of dimethyl acetylene dicarboxylate the product in the compound of formula (I) wherein X is a 4,5-bis-methoxycarbonyl-1,2,3-(1H)-triazole group. With ethyl propiolate the product is a mixture of the two possible positional isomers i.e. where X is 4- or 5-ethoxycarbonyl-1,2,3-(1H)-triazole, which can be separated by chromatography. Naturally these products can be converted to related triazole derivatives by employing conventional chemical transformation reactions. Thus reaction with concentrated ammonium hydroxide converts the esters to the corresponding amide derivatives. Similarly hydrolysis of the esters yields the corresponding acids. Decarboxylation of the resulting acids can be achieved, for example, by heating the acid with N,N-dimethylaniline, to yield the corresponding compound of formula (I) wherein X is an unsubstituted 1,2,3-triazole ring.

The azide (VII) is prepared by the syntheses previously described using as starting materials an ester of 2-azidoethoxyacetoacetic acid.

(d) In a further process, compounds of the formula (I) wherein X is a 1,2,4-(4H)-triazolering may be obtained by reacting an amine of the formula:

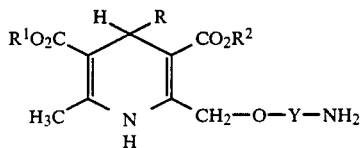 (VIII)

wherein R, R$^1$, R$^2$ and Y are as previously defined with N,N-dimethylformamide azine. The reaction is simply performed by heating the reactants, generally in equimolar quantities, in the presence of an acid, e.g. paratoluene sulphonic acid, in a reaction-inert organic solvent, e.g. toluene.

The amines of formula VIII are simply prepared from the azides of formula (VII) by reduction, for example using zinc dust or catalytic hydrogenation. In a typical procedure using zinc dust, the reaction is carried out in methanol and aqueous hydrochloric acid. Only short reaction times at room temperature are usually involved. Alternatively catalytic hydrogenation can be carried out in methanol in the presence of palladium on calcium carbonate at room temperature.

(e) In a further process compounds of the formula (I) wherein X is a 5-tetrazolyl ring are prepared from a compound of the formula:

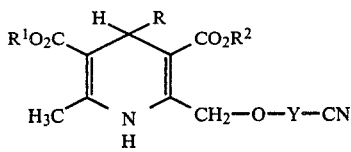 (IX)

wherein R, R$^1$, R$^2$ and Y are as previously defined, by reacting with tri-n-butyltin azide. The reaction is readily performed by warming the reactants together, generally in equimolar amounts, in an organic solvent e.g. dioxan. After a period of 12 to 24 hours under reflux, the solvent is evaporated, the product is taken up in diethyl ether and the resulting tin complex is decomposed with acid. The product is collected and purified by conventional techniques.

Substituted tetrazoles are prepared from the unsubstituted compounds by conventional chemical transformation reactions. Thus a conventional alkylation reaction, for example using an iodoalkane, yields the alkyl-tetrazoles as a mixture of positional isomers which can be separated by conventional techniques, for example by chromatography. Again reaction with a chloroformate or alkyl haloalkanoate, yields the alkoxycarbonyl and alkoxycarbonylalkyl derivatives respectively; thus reaction with methyl bromoacetate, for example, gives the two (methoxycarbonylmethyl)tetrazoles. Conventional chemical transformation reactions can be used to convert these to the corresponding acids, amides and nitriles.

The starting materials of formula (IX) are prepared by the Hantzsch synthesis described in (a) above but using a 4-(methoxycarbonylalkoxy)acetoacetate as the ketoester component. The resulting ester is converted to the amide and then the nitrile using conventional procedures.

(f) In an alternative process for the preparations of the formula (I) wherein X is a 2-thiazolyl group, a compound of the formula:

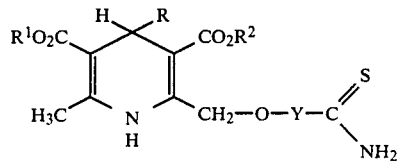 (X)

wherein R, R$^1$, R$^2$ and Y are as previously defined, is reacted with a haloaldehyde, haloketone or haloester of the formula:

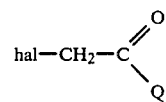 (XI)

wherein Q is H, C$_1$–C$_4$ lower alkyl, phenyl, benzyl or (CH$_2$)$_m$CO$_2$(C$_1$–C$_4$ lower alkyl) and hal is halogen, preferably bromine, to give compounds of the formula (I) wherein X is:

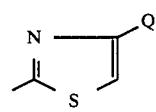 (XII)

and Q is as defined above. Naturally conventional chemical transformation reactions can again be used to obtain the acids, amides and nitriles from the esters where Q is (CH$_2$)$_m$CO$_2$(C$_1$–C$_4$ lower alkyl).

The reaction of the compound of formula (X) and the compound of formula (XI) is generally performed by heating the reactants together in more or less equimolar amounts in an organic solvent, e.g. ethanol. The reaction is complete after 5–10 hours under reflux and the reaction mixture is worked up and the product isolated and purified in a normal manner.

The thioamide starting materials of formula (X) are prepared from the corresponding amides in a conventional manner, for example using phosphorus pentasulphide, or better, para-methoxyphenylthionophosphine (Lawesson's reagent).

(g) In a further alternative process compounds of the formula (I) wherein X is a 3-amino-1,2,4-triazol-5-yl group may be prepared from a compound of the formula:

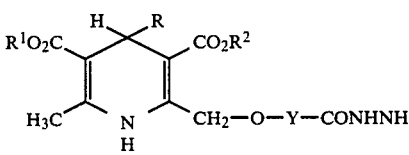 (XIII)

wherein R, R$^1$, R$^2$ and Y are as previously defined, by reacting with 2-methylisothiourea. The reaction is typically performed by heating a solution of 2-methylisothiourea sulphate and the hydrazine (XIII) in an organic solvent in the presence of an organic base. Butanol is a suitable solvent and after a period of 15–20 hours under reflux the product is isolated and purified by conventional techniques.

The hydrazines (XIII) are prepared using conventional techniques from the corresponding acids or esters.

(h) In a further process compounds of the formula (I) wherein X is a 1-(2,4,5-trimethyl-(1H)-imidazolyl) group are prepared from an amine of formula (VIII) by reacting with hexahydro-2,4,6-trimethyl-s-triazine (acetaldehyde ammonia). Alternatively the amine (VIII) is reacted with ethyl 2-amino-2-cyanoacetate and trimethyl orthoformate to give the compound (I) wherein X is the 1-(5-amino-4-ethoxycarbonylimidazolyl) group.

(i) In a further process, compounds of the formula (I) wherein X is an oxadiazolyl or thiadiazolyl group are prepared from a compound of the formula:

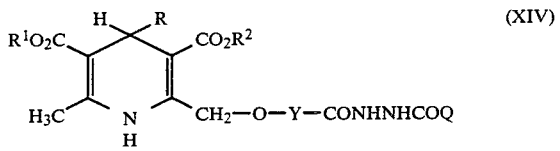

where Q is as previously defined by reacting with phosphorus pentoxide to give the compound wherein X is a 2-(1,3,4-oxadiazolyl) ring or with para-methoxyphenylthionophosphine (Lawesson's reagent) to give the compound wherein X is a 2-(1,3,4-thiadiazolyl) ring. Again conventional hydrolysis, amidation and dehydration reactions may be used to obtain the acids, esters and nitriles from the esters where Q is $(CH_2)_mCO_2(C_1-C_4$ lower alkyl).

The compounds (XIV) are prepared from the corresponding acid in a conventional manner, for example by reacting with acetylhydrazine in the presence of carbonyldiimidazole.

(j) In a further process compounds of the formula (I) wherein X is a 2-(5-amino-1,3,4-thiadiazolyl) group are prepared from a compound of the formula:

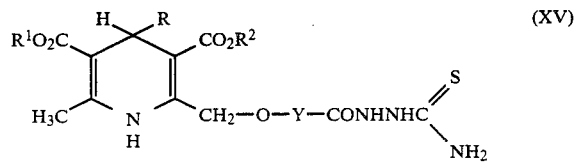

by reaction with phosphorus oxychloride. The reaction is simply performed by stirring the thiosemicarbazide (XV) in excess phosphorus oxychloride at room temperature for several hours and the product is isolated, after evaporation of excess phosphorus oxychloride, by conventional procedures.

The thiosemicarbazides (XV) are again prepared from the corresponding acids, for example by reacting with thiosemicarbazide and carbonyldiimidazole.

(k) In a further process compounds of the formula (I) where X is a 2,5-dimethylpyrrole are prepared from an amine of formula (VIII) by reacting with hexane-2,5-dione. The reaction is performed by warming the reagents in approximately equimolar amounts in an organic solvent with a trace of acid present. The water formed by the reaction can be removed azeotropically by refluxing in benzene to assist the reaction. Finally the product is isolated and purified using conventional techniques.

The ability of the compounds to inhibit the movement of calcium into the cell is shown by their effectiveness in reducing the response of isolated heart tissue to an increase in calcium ion concentration in vitro. The test is performed by mounting spirally cut strips of rat aorta with one end fixed and the other attached to a force transducer. The tissue is immersed in a bath of physiological saline solution containing potassium ions at a concentration of 45 millimolar and no calcium. Calcium chloride is added to the bath with a pipette to give a final calcium ion concentration of 2 millimolar. The change in tension caused by the resulting contraction of the tissue is noted. The bath is drained and replaced with fresh saline solution and, after 45, minutes the test is repeated with the particular compound under test present in the saline solution. The concentration of compound required to reduce the response by 50% is recorded.

The antihypertensive activity of the compounds is also evaluated after oral administration by measuring the fall in blood pressure in spontaneously hypertensive rats or renally hypertensive dogs.

For administration to man in the curative or prophylactic treatment of cardiac conditions and hypertension, oral dosages of the compounds are generally in the range of from 2-100 mg daily for an average adult patient (70 kg). Thus for a typical adult patient, individual tablets or capsules contain from 1 to 10 mg of active compound in a suitable pharmaceutically acceptable vehicle or carrier. Dosages for intravenous administration are typically within the range 1 to 10 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

For human use, the compounds of the formula (I) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic.

Thus in a further aspect the invention provides a pharmaceutical composition comprising a compound of the formula (I), or a pharmaceutically acceptable acid addition salt thereof, together with a pharmaceutically acceptable diluent or carrier.

The invention thus provides a compound of the formula (I) or a pharmaceutically acceptable acid addition salt thereof, for use in the treatment of cardiovascular conditions including use in the prevention or treatment of cardiac conditions, or use as an antihypertensive, in man.

The invention also provides a method of protecting the heart from the deleterious effects of ischaemia, which comprises administering an effective amount of a compound of the formula (I) or pharmaceutically acceptable acid addition salt thereof, or pharmaceutical composition as defined above.

The invention also includes a method of treating hypertension which comprises administering an antihypertensive amount of a compound of the formula (I) or pharmaceutically acceptable acid addition salt thereof, or pharmaceutical composition as defined above.

The following Examples illustrate the invention:

EXAMPLE 1

4-(2-Chlorophenyl)-3-ethoxycarbonyl-5-methoxycarbonyl-6-methyl-2-[2-(2,4,5-trimethyl-1-imidazolyl)ethoxymethyl]-1,4-dihydropyridine, hydrochloride salt Ethyl 4-[2-(2,4,5-trimethyl-1-imidazolyl)ethoxy]acetoacetate (6.4 g), 2-chlorobenzaldehyde (3.2 g), methyl 3-aminocrotonate (2.6 g) and acetic acid (1 ml) in ethanol (15 ml) were mixed and heated under reflux for 4.5 hours. The cooled reaction mixture was then evaporated to dryness and the residue partitioned between 2N hydrochloric acid (100 ml) and toluene (50 ml). The acid layer was separated, extracted with methylene chloride (3×20 ml) and the extracts were washed with saturated aqueous sodium carbonate (30 ml), dried ($Na_2CO_3$), filtered, and evaporated. The residue in a little toluene was chromatographed on silica (t.l.c. grade, 4 g), eluting with methylene chloride plus 30% v/v petrol. Appropriate fractions were combined, evaporated to dryness and redissolved in ethyl acetate. Addition of ethereal hydrogen chloride precipitated the hydrochloride salt, which was recrystallised from ethyl acetate to give the title compound (1.2 g), m.p. 167°–8° C.

Analysis %: Found: C, 57.30; H, 6.07; N, 7.76, $C_{26}H_{32}ClN_3O_5.HCl$ requires: C, 57.99; H, 6.18; N, 7.80.

EXAMPLE 2

Diethyl 4-(2-chlorophenyl)-2-[2-(1-imidazolyl)ethoxymethyl]-6-methyl-1,4-dihydropyridine-3,5-dicarboxylate was prepared by the method described in Example I but starting with ethyl instead of methyl 3-aminocrotonate and ethyl 4-[2-(1-imidazolyl)ethoxy]acetoacetate instead of ethyl 4-[2-(2,4,5-trimethyl-1-imidazolyl)ethoxy]acetoacetate. The product was characterised as an oxalate salt, m.p. 163°–5° C.

Analysis %: Found: C, 54.89; H, 5.22; N, 7.41. $C_{24}H_{28}ClN_3O_5.C_2H_2O_4$ requires: C, 55.37; H, 5.36; N, 7.45.

EXAMPLE 3

4-(2-Chlorophenyl)-3-ethoxycarbonyl-5-methoxycarbonyl-6-methyl-2-[(1-methyl-2-imidazolyl)methoxymethyl]-1,4-dihydropyridine Ethyl 4-(1-methyl-2-imidazolylmethoxy)acetoacetate (crude, 12 g) and ammonium acetate (4 g) in ethanol (40 ml) were heated gently under reflux for 20 minutes. Then methyl 2-(2-chlorobenzylidene)acetoacetate (13 g) was added and heating under reflux was continued for 4 hours. The cooled reaction mixture was evaporated to dryness and the residue dissolved in toluene (150 ml) and washed with 10% sodium hydroxide solution to remove acetic acid. The toluene solution was extracted with 2N hydrochloric acid (150 ml and 50 ml), the combined acid extracts washed with fresh toluene (50 ml) and the pH of the aqueous solution was adjusted to 3–4 with aqueous sodium carbonate. The aqueous solution was extracted with ethyl acetate (2×200 ml). These extracts were dried ($Na_2CO_3$) and the solution was filtered and evaporated to dryness. The residue, in a little toluene, was chromatographed on silica (t.l.c. grade, 17 g), eluting with petrol plus 30% v/v methylene chloride initially, changing gradually to 100% methylene chloride. Appropriate fractions were combined, evaporated, and the residue crystallized from diethyl ether plus a little petrol. Recrystallisation from ethyl acetate and petrol (1:1) gave the title compound (1 g), m.p. 137°–8° C.

Analysis %: Found: C, 60.41; H, 5.78; N, 9.11. $C_{23}H_{26}ClN_3O_5$ requires: C, 60.06; H, 5.70; N, 9.14.

EXAMPLES 4–10

The following compounds were prepared by the method described in Example 3 with appropriate starting materials and were characterised in the form indicated.

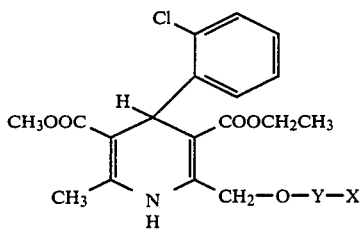

| Example No. | Y | X | Form characterised | m.p. (°C.) | Analysis % (Theoretical in brackets) C | H | N |
|---|---|---|---|---|---|---|---|
| 4 | —CH₂CH₂— | —N⟨CH₃ imidazolyl⟩ | hydrochloride | 139 | 53.96 (53.70 | 5.57 5.68 | 7.96 8.17) |
| 5 | —CH₂CH₂— | —N⟨CH₃ imidazolyl⟩ | free base | 144–5 | 60.69 (60.82 | 6.07 5.95 | 8.94 8.87) |

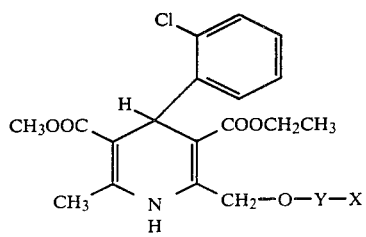

| Example No. | Y | X | Form characterised | m.p. (°C.) | Analysis % (Theoretical in brackets) C | H | N |
|---|---|---|---|---|---|---|---|
| 6 | —CH₂— | (4-dimethylamino-methylpyridine) | oxalate, hydrate | 147 | 55.48 (55.30 | 5.42 5.64 | 7.12 6.91) |
| 7 | —CH₂— | (2-pyridyl) | free base | 115 | 63.26 (63.08 | 5.50 5.51 | 6.04 6.13) |
| 8 | —CH₂CH— \| CH₃ | (2-methylimidazol-1-yl) | hydrochloride | ca. 100 | Characterised by N.m.r. spectra (below) | | |
| 9 | —(CH₂)₃— | (2,4,5-trimethylimidazol-1-yl) | free base | oil | | | |
| 10 | —CH₂— | (1-benzylimidazol-2-yl) | free base | oil | | | |

N.m.r. spectra in CDCl₃, δ values:

Example 8: 8.22 (1H, br, NH); 6.9–7.7 (6H, m); 5.33 (1H, s); 4.63 (2H, s); 3.6–4.2 (5H, m); 3.52 (3H, s); 2.75 (3H, s); 2.31 (3H, s); 1.51 (3H, d, J 7 Hz); 1.15 (3H, t, J 6.5 Hz).

Example 9: 6.95–7.5 (4H, m); 5.41 (1H, s); 4.69 (2H, s); 3.5–4.3 (6H, m); 3.58 (3H, s); 2.30 (6H, s); 2.07 (6H, s); 1.95 (2H, m); 1.16 (3H, t, J 7 Hz).

Example 10: 6.8–7.5 (12H, m); 5.40 (1H, s); 5.17 (2H, s); 4.75 (2H, s); 4.60 (2H, s); 4.03 (2H, q, J 7 Hz); 3.59 (3H, s); 2.26 (3H, s); 1.16 (3H, t, J 7 Hz).

EXAMPLE 11

4-(2-Chlorophenyl)-3-ethoxycarbonyl-2-[(2-imidazolyl)methoxymethyl]-5-methoxycarbonyl-6-methyl-1,4-dihydropyridine, hydrochloride salt 4-(2-Chlorophenyl)-2-[(1-benzyl-2-imidazolyl)methoxymethyl]-3-ethoxycarbonyl-5-methoxycarbonyl-6-methyl-1,4-dihydropyridine (Example 10) (2 g) was dissolved in ethanol (70 ml) and acidified with hydrogen chloride gas. Then 10% palladium on charcoal catalyst (0.25 g) was added and the suspension was stirred under hydrogen at 50 p.s.i. and room temperature overnight. Examination of the reaction mixture by t.l.c. showed that about one third of the starting material had been converted to a more polar product. The catalyst was removed by filtration, the ethanol was evaporated and the residue partitioned between chloroform (50 ml) and dilute aqueous ammonia (30 ml). The chloroform solution was dried (Na₂CO₃), filtered and evaporated. The residue was dissolved in a little toluene and chromatographed on silica (t.l.c. grade, 6 g). Elution with toluene removed unreacted starting material; elution with chloroform and then chloroform plus 2–4% v/v methanol gave the product, which was converted to the hydrochloride salt by addition of ethereal hydrogen chloride to an acetone solution of the free base. Recrystallisation of the hydrochloride salt from methanol-ethyl acetate (1:4) gave the title compound (430 mg), m.p. 190° C.

Analysis %: Found: C, 54.75; H, 5.32; N, 8.71. C₂₂H₂₄ClN₃O₅.HCl requires: C, 54.28; H, 5.22; N, 8.71.

EXAMPLE 12

4-(2,3-Dichlorophenyl)-3-ethoxycarbonyl-5-methoxycarbonyl-6-methyl-2-[2-(2,4,5-trimethyl-1-imidazolyl)ethoxymethyl]-1,4-dihydropyridine A solution of 2,3-dichlorobenzaldehyde (8.75 g), methyl 3-aminocrotonate (5.75 g) and ethyl 4-[2-(2,4,5- trimethyl-1-imidazolyl)ethoxy]acetoacetate (14.1 g) in 50 ml of methanol was stirred at reflux temperature for 5 hours. After evaporation to dryness, the residue was dissolved in 2N hydrochloric acid (200 ml) and washed with diethyl ether (3×100 ml) followed by extraction with methylene chloride (4×150 ml). The combined methylene chloride extracts were washed with saturated aqueous sodium carbonate solution (2×200 ml), dried ($Na_2CO_3$), filtered and evaporated to give a beige solid (12.5 g). The crude product was chromatographed on silica (40 g), eluting with ethyl acetate. The appropriate fractions were combined and evaporated and the resultant oil (2.1 g) crystallised from diethyl ether (10 ml) to give the title compound, (1.5 g), m.p. 123°–125° C.

Analysis %: Found: C, 58.21; H, 5.83; N, 7.83. $C_{26}H_{31}Cl_2N_3O_5$ requires: C, 58.01; L H, 5.80; N, 7.88.

EXAMPLE 13

4,5-Bis(methoxycarbonyl)-1-<2-{[4-(2-chlorophenyl)-3-ethoxycarbonyl-5-methoxycarbonyl-6-methyl-1,4-dihydropyridin-2-yl]methoxy}ethyl>-1,2,3-(1H)-triazole A solution of dimethyl acetylenedicarboxylate (0.35 g) and 2-(2-azidoethoxy)methyl-4-(2-chlorophenyl)-3-ethoxycarbonyl-5-methoxycarbonyl-6-methyl-1,4-dihydropyridine (0.87 g) in toluene (40 ml) was heated under reflux for 4 hours and then evaporated. The residue was chromatographed on silica (10 g), eluting with dichloromethane plus 0–2% v/v methanol. Appropriate fractions were combined and evaporated and the residue triturated with diethyl ether. The resulting solid was collected, washed with diethyl ether and dried to give the title compound (0.91 g), m.p. 80° C.

Analysis %: Found: C, 54.20; H, 5.33; N, 9.67. $C_{26}H_{29}ClN_4O_9$ requires: C, 54.12; H, 5.07; N, 9.71.

EXAMPLES 14–17

The method of Example 13 was used but starting with ethyl propiolate and 2-(2-azidoethoxy)methyl-4-(2-chlorophenyl)-3-ethoxycarbonyl-5-methoxycarbonyl-6-methyl-1,4-dihydropyridine or 2-(2-azidoethoxy)methyl-4-(2,3-dichlorophenyl)-3-ethoxycarbonyl-5-methoxycarbonyl-6-methyl-1,4-dihydropyridine, respectively. In each case two isomers were produced which were separated by column chromatography on silica.

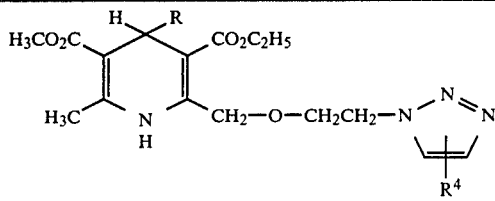

| Example No. | R | $R^4$ | m.p. (°C.) | Analysis % (Theoretical in brackets) | | |
|---|---|---|---|---|---|---|
| | | | | C | H | N |
| 14 | ⌬-Cl | 4-$CO_2CH_2CH_3$ | 116–118 | 55.91 (56.34 | 5.54 5.48 | 10.92 10.51) |
| 15 | ⌬-Cl | 5-$CO_2CH_2CH_3$ | 146–147 | 56.41 (56.34 | 5.56 5.48 | 10.51 10.51) |
| 16 | ⌬-Cl,Cl | 4-$CO_2CH_2CH_3$ | 134–136 | 53.12 (52.92 | 5.18 4.97 | 9.92 9.87) |
| 17 | ⌬-Cl,Cl | 5-$CO_2CH_2CH_3$ | 147–148 | 52.86 (52.92 | 5.05 4.97 | 10.02 9.87) |

EXAMPLE 18

4,5-Bis(carbamoyl)-1-<2-{[4-(2-chlorophenyl)-3-ethoxycarbonyl-5-methoxycarbonyl-6-methyl-1,4-dihydropyridin-2-yl]methoxy}ethyl>-1,2,3-(1H)-triazole A solution of 4,5-bis(methoxycarbonyl)-1-<2{[4-(2-chlorophenyl)-3-ethoxycarbonyl-5-methoxycarbonyl-6-methyl-1,4-dihydropyridin-2-yl]methoxy}ethyl>-1,2,3-(1H)-triazole (Example 13) (0.48 g) in dioxane (10 ml) was treated with concentrated aqueous ammonia solution (10 ml, specific gravity 0.880) and the mixture was stirred at room temperature for 2 hours and then evaporated. The residue was partitioned between ethyl acetate and water and the separated organic layer was dried ($Na_2SO_4$) and evaporated. The residual solid was washed with diethyl ether and dried to give the title compound (0.32 g), m.p. 202°–204° C.

Analysis %: Found: C, 52.52; H, 5.03; N, 15.15. $C_{24}H_{27}ClN_6O_7$ requires: C, 52.70; H, 4.98; N, 15.37.

EXAMPLES 19–22

The following compounds were prepared by the method described in Example 18 starting with the appropriate ethoxycarbonyltriazole.

| Example No. | R | $R^4$ | m.p. (°C.) | Analysis % (Theoretical in brackets) | | |
|---|---|---|---|---|---|---|
| | | | | C | N | N |
| 19 | ⌬-Cl | 4-$CONH_2$ | 215–217 | 54.70 (54.82 | 5.30 5.20 | 13.86 13.90) |

-continued

[Structure: H3CO2C and CO2C2H5 groups on a 1,4-dihydropyridine ring with H3C and NH, and CH2-O-CH2CH2-N linked to a triazole ring bearing R4]

| Example No. | R | R⁴ | m.p. (°C.) | Analysis % (Theoretical in brackets) C | N | N |
|---|---|---|---|---|---|---|
| 20 | 2-chlorophenyl | 5-CONH₂ | 125–128 | 54.49 (54.82 | 5.32 5.20 | 13.33 13.90) |
| 21 | 2,3-dichlorophenyl | 4-CONH₂ | 148–151 | 51.27 (51.31 | 4.79 4.68 | 13.11 13.01) |
| 22 | 2,3-dichlorophenyl | 5-CONH₂ | 163–166 | 51.37 (51.31 | 4.81 4.68 | 13.20 13.01) |

EXAMPLE 23

4-Carboxy-1-<2-{[4-(2-chlorophenyl)-3-ethoxycarbonyl-5-methoxycarbonyl-6-methyl-1,4-dihydropyridin-2-yl]methoxy}ethyl>-1,2,3-(1H)-triazole 1M Aqueous sodium hydroxide solution (5 ml) was added to a suspension of 1-<2-{[4-(2-chlorophenyl)-3-ethoxycarbonyl-5-methoxycarbonyl-6-methyl-1,4-dihydropyridin-2-yl]methoxy}ethyl>-4-ethoxycarbonyl-1,2,3-(1H)-triazole (Example 14) (0.53 g) in dioxane (20 ml) and the mixture was stirred at room temperature for 2 hours and then evaporated to dryness. The residue was treated with acetic acid (1 ml) and partitioned between ethyl acetate and water. The organic layer was washed with water, dried (Na₂SO₄), and evaporated. The residue was triturated with ethyl acetate and the resulting solid collected, washed with ethyl acetate and dried to give the title compound (0.42 g), m.p. 184°–185° C. (decomp.).

Analysis %: Found: C, 54.43; H, 5.05; N, 11.09. $C_{23}H_{25}ClN_4O_7$ requires: C, 54.71; H, 4.99; N, 11.10.

EXAMPLE 24

5-Carboxy-1-<2-{[4-(2-chlorophenyl)-3-ethoxycarbonyl-5-methoxycarbonyl-6-methyl-1,4-dihydropyridin-2-yl]methoxy}ethyl>-1,2,3-(1H)-triazole was prepared by the method described in Example 23 using 1-<2-{[4-(2-chlorophenyl)-3-ethoxycarbonyl-5-methoxycarbonyl-6-methyl-1,4-dihydropyridin-2-yl]methoxy}ethyl>-5-ethoxycarbonyl-1,2,3-(1H)-triazole. The product had m.p. 180°–181° C. decomp.

Analysis %: Found: C, 54.43; H, 5.05; N, 11.09. $C_{23}H_{25}ClN_4O_7$ requires: C, 54.71; L H, 4.99; N, 11.10.

EXAMPLE 25

1-<2-{[4-(2-Chlorophenyl)-3-ethoxycarbonyl-5-methoxycarbonyl-6-methyl-1,4-dihydropyridin-2-yl]methoxy}ethyl>-1,2,3-(1H)-triazole A solution of 4-carboxy-1-<2-{[4-(2-chlorophenyl)-3-ethoxycarbonyl-5-methoxycarbonyl-6-methyl-1,4-dihydropyridin-2-yl]methoxy}ethyl>-1,2,3-(1H)-triazole (Example 23) (0.48 g) in N,N-dimethylaniline (10 ml) was heated under reflux for 15 minutes, allowed to cool to room temperature, and chromatographed on silica (t.l.c. grade, 100 g), eluting with dichloromethane plus 0–4% v/v methanol. Appropriate fractions were combined and evaporated and the residue triturated with diethyl ether. The resulting solid was collected, washed with diethyl ether, and dried to give the title compound (0.25 g), m.p. 134°–140° C.

Analysis %: Found: C, 57.24; H, 5.59; N, 12.55. $C_{22}H_{25}ClN_4O_5$ requires: C, 57.33; H, 5.49; N, 12.16.

EXAMPLE 26

1-<2-{[4-(2,3-Dichlorophenyl)-3-ethoxycarbonyl-5-methoxycarbonyl-6-methyl-1,4-dihydropyridin-2-yl]methoxy}ethyl>-1,2,3-(1H)-triazole 1M Aqueous sodium hydroxide solution (10 ml) was added to a solution of 1-<2-{[4-(2,3-dichlorophenyl)-3-ethoxycarbonyl-5-methoxycarbonyl-6-methyl-1,4-dihydropyridin-2-yl]methoxy}ethyl>-4ethoxycarbonyl-1,2,3-(1H)-triazole (Example 16) (0.96 g) in dioxane (25 ml) and the mixture stirred at room temperature for 1.75 hours and then evaporated. The residue was dissolved in water, treated with acetic acid (2 ml), and extracted into ethyl acetate. The ethyl acetate extract was washed with water, dried (Na₂SO₄) and evaporated. The residue was dissolved in N,N-dimethylaniline (5 ml) and the solution heated under reflux for 15 minutes, allowed to cool to room temperature and chromatographed on silica (t.l.c. grade, 100 g), eluting with dichloromethane plus 0–2% v/v methanol. Appropriate fractions were combined and evaporated and the residue triturated with diethyl ether. The resulting solid was collected, washed with diethyl ether and dried to give the title compound (0.54 g), m.p. 155°–156° C.

Analysis %: Found: C, 53.30; H, 5.10; N, 11.34. $C_{22}H_{24}Cl_2N_4O_5$ requires: C, 53.34; H, 4.88; N, 11.31.

EXAMPLE 27

4-<2-{[4-(2-Chlorophenyl)-3-ethoxycarbonyl-5-methoxycarbonyl-6-methyl-1,4-dihydropyridin-2-yl]methoxy}ethyl>-1,2,4-(4H)-triazole A solution of 2-(2-aminoethoxy)methyl-4-(2-chlorophenyl)-3-ethoxycarbonyl-5-methoxycarbonyl-6-methyl-1,4-dihydropyridine (1.02 g), N,N-dimethylformamide azine (0.36 g) and para-toluene sulphonic acid (0.30 g) in toluene (25 ml) was heated under reflux for 7 hours and then evaporated. The residue was partitioned between ethyl acetate and 10% aqueous sodium carbonate solution and the organic layer separated, dried (Na₂SO₄) and evaporated to give the title compound (0.54 g), m.p. 141°–143° C. This product was characterised containing 0.25 molar equivalents of water of hydration.

Analysis %: Found: C, 56.86; H, 5.70; N, 11.52. $C_{22}H_{25}ClN_4O_5$ requires: C, 56.77; H, 5.38; N, 12.04.

EXAMPLE 28

4-<2-{[4-(2,3-Dichlorophenyl)-3-ethoxycarbonyl-5-methoxycarbonyl-6-methyl-1,4-dihydropyridin-2-yl]methoxy}ethyl>-1,2,4-(4H)-triazole was prepared by the method of Example 27 but using 2-(2-aminoethoxy)methyl-4-(2,3-dichlorophenyl)-3-ethoxycarbonyl-5-methoxycarbonyl-6-methyl-1,4-dihydropyridine as starting material. The product had m.p. 86°–88° C.

Analysis %: Found: C, 53.17; H, 5.20; N, 10.91. $C_{22}H_{24}Cl_2N_4O_5$ requires: C, 53.34; H, 4.85; N, 11.31.

EXAMPLE 29

1-<2-{[4-(2-Chlorophenyl)-3-ethoxycarbonyl-5-methyoxycarbonyl-6-methyl-1,4-dihydropyridin-2-yl]methoxy}ethyl>-4-cyano-1,2,3-(1H)-triazole A solution of trifluoroacetic anhydride (0.26 g) in dioxane (5 ml) was added to a stirred, ice-cooled solution of 4-carboxamido-1-<2-{[4-(2-chlorophenyl)-3-ethoxycarbonyl-5-methoxycarbonyl-6-methyl-1,4-dihydropyridin-2-yl]methoxy}ethyl>-1,2,3-(1H)-triazole (Example 19, 0.55 g) and pyridine (0.18 g) in dioxane (20 ml) and the mixture was stirred at room temperature for five days, diluted with water and extracted into ethyl acetate. The ethyl acetate extract was washed with water, dried ($Na_2SO_4$) and evaporated. The residual oil was purified by chromatography on silica (t.l.c. grade, 5 g), eluting with dichloromethane plus 25% v/v n-hexane. Appropriate fractions were combined and evaporated. The residual oil was crystallised from diisopropyl ether to give the title compound (0.09 g), m.p. 116° C.

Analysis %: Found: C, 56.53; H, 5.02; N, 14.15. $C_{23}H_{23}ClN_5O_5$ requires: C, 56.84; H, 4.98; N, 14.41.

EXAMPLE 30

5-{[4-(2,3-Dichlorophenyl)-3-ethoxycarbonyl-5-methoxycarbonyl-6-methyl-1,4-dihydropyridin-2-yl]methoxymethyl]tetrazole A solution of [4-(2,3-dichlorophenyl)-3-ethoxycarbonyl-5-methoxycarbonyl-6-methyl-1,4-dihydropyridin-2-yl]methoxyacetonitrile (3.52 g) and tri-n-butyltin azide (3.00 g) in dioxane (100 ml) was heated under reflux for 21.5 hours and then evaporated. The residual oil was taken up in diethyl ether (200 ml) and dry halogen chloride was bubbled through the stirred solution in a slow stream for 50 minutes. The resulting precipitate was collected, washed with diethyl ether and dried to give the title compound (3.14 g), m.p. 112°–114° C.

Analysis %: Found: C, 50.08; H, 4.41; N, 14.76. $C_{20}H_{21}Cl_2N_5O_5$ requires: C, 49.80; H, 4.39; N, 14.52.

EXAMPLE 31

5-{[4-(2-Chlorophenyl)-3-ethoxycarbonyl-5-methoxycarbonyl-6-methyl-1,4-dihydropyridin-2-yl]methoxymethyl}tetrazole was prepared by the method of Example 30 but using [4-(2-chlorophenyl)-3-ethoxycarbonyl-5-methoxycarbonyl-6-methyl-1,4-dihydropyridin-2-yl]methoxyacetonitrile as starting material. The product was obtained as a hemihydrate, m.p. 122°–124° C.

Analysis %: Found: C, 52.52; H, 4.85; N, 15.51 $C_{20}H_{22}ClN_5O_5.0.5H_2O$ requires: C, 52.58; H, 5.07; N, 15.33.

EXAMPLES 32 AND 33

5-{[4-(2,3-Dichlorophenyl)-3-ethoxycarbonyl-5-methoxycarbonyl-6methyl-1,4-dihydropyridin-2-yl]methoxymethyl}-1-methyl-(1H)-tetrazole and 5-{[4-(2,3-dichlorophenyl)-3-ethoxycarbonyl-5-methoxycarbonyl-6-methyl-1,4-dihydropyridin-2-dihydropyridin-2-yl]methoxymethyl}-2-methyl-(2H)-tetrazole A mixture of 5-{[4-(2,3-dichlorophenyl)-3-ethoxycarbonyl-5-methoxycarbonyl-6-methyl-1,4-dihydropyridin-2-yl]methoxymethyl}-tetrazole (0.96 g), iodomethane (;b 0.72 g) and potassium carbonate (0.69 g) in acetonitrile (40 ml) was heated under reflux for 8 hours, filtered and evaporated. The residual oil was separated into two components by chromatography on silica (t.l.c. grade 10 g), eluting with dichloromethane plus 0–50% v/v ethyl acetate. In each case the appropriate fractions were combined and evaporated and the residual oil triturated with diethyl ether. The resulting solid was collected, washed with diethyl ether and dried to give each of the title compounds:

(i) The less polar 2-isomer (229 mg) had m.p. 141°–142° C.

Analysis %: Found: C, 50.55; H, 4.35; N, 14.29. $C_{21}H_{23}Cl_2N_5O_5$ requires: C, 50.82; H, 4.67; N, 14.11.

(ii) The more polar 1-isomer (228 mg) had m.p. 62°–64° C.

Analysis %: Found: C, 50.71; H, 4.74; N, 14.13. $C_{21}H_{23}Cl_2N_5O_5$ requires: C, 50.82; H, 4.67; N, 14.11.

EXAMPLES 34–39

The following compounds were prepared by the method described in Examples 32 and 33 using the appropriate dihydropyridine and reacting with iodomethane or methyl bromoacetate. In each case the two isomers produced were separated by chromatography on silica and the more polar assigned as the 1-isomer.

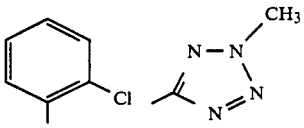

| Example No. | R | $R^5$ | m.p. (°C.) | Analysis % (Theoretical in brackets) C | H | N |
|---|---|---|---|---|---|---|
| 34 | 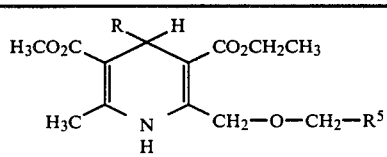 | CH₃ | 138–139 | 54.76 (54.60 | 5.47 5.24 | 14.85 15.16) |

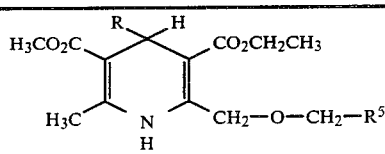

| Example No. | R | R⁵ | m.p. (°C.) | C | H | N |
|---|---|---|---|---|---|---|
| 35 | 2-chlorophenyl | 1-methyl-tetrazol-5-yl (N-N=N-N(CH₃)) | 122–124 | 54.44 (54.60 | 5.41 5.24 | 14.98 15.16) |
| 36 | 2,3-dichlorophenyl | 1-(methoxycarbonylmethyl)-tetrazol-5-yl | 183–185 | 49.75 (49.83 | 4.65 4.55 | 12.55 12.63) |
| 37 | 2,3-dichlorophenyl | 2-(methoxycarbonylmethyl)-tetrazol-5-yl | 185–187 | 49.80 (49.83 | 4.47 4.55 | 12.71 12.63) |
| 38 | 2-chlorophenyl | 1-(methoxycarbonylmethyl)-tetrazol-5-yl | Oil | Characterised by N.m.r. spectra | | |
| 39 | 2-chlorophenyl | 2-(methoxycarbonylmethyl)-tetrazol-5-yl | 164–166 | Characterised by N.m.r. spectra | | |

EXAMPLE 40

2-Carbamoylmethyl-5-{[4-(2-chlorophenyl)-3-ethoxycarbonyl-5-methoxycarbonyl-6-methyl-1,4-dihydropyridin-2-yl]methoxymethyl}-(2H)-tetrazole A mixture of 5-{[4-(2-chlorophenyl)-3-ethoxycarbonyl-5-methoxycarbonyl-6-methyl-1,4-dihydropyridin-2-yl]methoxymethyl}-2-methoxycarbonylmethyl-(2H)-tetrazole (0.52 g), dioxane (15 ml) and 0.880 aqueous ammonium hydroxide solution (10 ml) was stirred at room temperature for 2.5 hours and then evaporated. The residual oil was partitioned between water and ethyl acetate and the organic layer washed with water, dried (Na₂SO₄) and evaporated. The residual oil was triturated with diethyl ether and the resulting solid collected, washed with diethyl ether and dried to give the title compound (0.31 g), m.p. 101°–103° decomp.

Analysis %: Found: C, 52.54; H, 5.01; N, 16.64. C₂₂H₂₅ClN₆O₆ requires: C, 52.33; H, 4.99; N, 16.64.

EXAMPLE 41

1-Carbamoylmethyl-5-{[4-(2-chlorophenyl)-3-ethyoxycarbonyl-5-methoxycarbonyl-6-methyl-1,4-dihydropyridin-2-yl]methoxymethyl}-(1H)-tetrazole was prepared by the method of Example 40 but using 5-{[4-(2-chlorophenyl)-3-ethoxycarbonyl-5-methoxycarbonyl-6-methyl-1,4-dihydropyridin-2-yl]methoxymethyl}-1-methoxycarbonylmethyl-(1H)-tetrazole as starting material. The product had m.p. 97°–100° C.

Analysis %: Found: C, 52.08; H, 5.10; N, 16.48. C₂₂H₂₅ClN₆O₆ requires: C, 52.33; H, 4.99; N, 16.64.

EXAMPLE 42

2-Carbamoylmethyl-5-{[4-(2,3-dichlorophenyl)-3-ethoxycarbonyl-5-methoxycarbonyl-6-methyl-1,4-dihydropyridin-2-yl]methoxymethyl}-(2H)-tetrazole was prepared by the method of Example 40 but using 5-{[4-(2,3-dichlorophenyl)-3-ethoxycarbonyl-5-methoxycarbonyl-6-methyl-1,4-dihydropyridin-2-yl]methoxymethyl}-2-methoxycarbonylmethyl-(2H)-tetrazole as starting material. The product had m.p. 130°–132° C.

Analysis %: Found: C, 48.79; H, 4.50; N, 15.57. C₂₂H₂₄Cl₂N₆O₆ requires: C, 48.99; H, 4.49; N, 15.58.

EXAMPLE 43

1-Carbamoylmethyl-5-{[4-(2,3-dichlorophenyl)-3-ethoxycarbonyl-5-methoxycarbonyl-6-methyl-1,4-dihydropyridin-2-yl]methoxymethyl}-(1H)-tetrazole was prepared by the method of Example 40 but using 5-{[4-(2,3-dichlorophenyl)-3-ethoxycarbonyl-5-methoxycarbonyl-6-methyl-1,4-dihydropyridin-2-yl]methoxymethyl}-1-methoxycarbonylmethyl-(1H)-tetrazole as starting material. The product had m.p. 206°–208° C. decomp.

Analysis %: Found: C, 49.25; H, 4.69; N, 15.27. $C_{22}H_{24}Cl_2N_6O_6$ requires: C, 48.99; H, 4.49; N, 15.58.

EXAMPLE 44

2-{[4-(2-Chlorophenyl)-3-ethoxycarbonyl-5-methoxycarbonyl-6-methyl-1,4-dihydropyridin-2-yl]methoxymethyl}-4-methylthiazole A solution of 2-{[4-(2-chlorophenyl)-3-ethoxycarbonyl-5-methoxycarbonyl-6-methyl-1,4-dihydropyridin-2-yl]methoxy}-thioacetamide (0.44 g) and chloroacetone (0.30 g) in ethanol (30 ml) was heated under reflux for 7 hours and then evaporated. The residual oil was purified by chromatography on silica (t.l.c. grade, 10 g) using dichloromethane plus 0–10% v/v ethyl acetate as eluant. Appropriate fractions were combined and evaporated and the residue triturated with diisopropyl ether. The resulting solid was collected, washed with petroleum ether (b.p. 60°–80° C.) and dried to give the title compound (78 mg), m.p. 107°–110° C.

Analysis %: Found: C, 57.83; H, 5.56; N, 5.83. $C_{23}H_{25}ClN_2O_5S$ requires: C, 57.92; H, 5.28; N, 5.87.

EXAMPLE 45

2-{[4-(2-Chlorophenyl)-3-ethoxycarbonyl-5-methoxycarbonyl-6-methyl-1,4-dihydropyridin-2-yl]methoxymethyl}-4-ethoxycarbonylthiazole was prepared by the method of Example 44 but using ethyl 3-bromopyruvate instead of chloroacetone. The product had m.p. 111°–113° C.

Analysis %: Found: C, 56.53; H, 5.28; N, 5.16. $C_{25}H_{27}ClN_2O_7S$ requires: C, 56.13; H, 5.09; N, 5.24.

EXAMPLE 46

2-{[4-(2,3-Dichlorophenyl)-3-ethoxycarbonyl-5-methoxycarbonyl-6-methyl-1,4-dihydropyridin-2-yl]methoxymethyl}-4-ethoxycarbonylthiazole was prepared by the method of Example 44 but using 2-{[4-(2,3-dichlorophenyl)-3-ethoxycarbonyl-5-methoxycarbonyl-6-methyl-1,4-dihydropyridin-2-yl]methoxy}-thioacetamide and ethyl 3-bromopyruvate as starting materials.

This product was obtained as an oil and it was characterised by its N.m.r. spectrum in CDCl₃, δ values: 8.21 (1H,s); 6.85–7.44 (4H,m); 5.47 (1H,s); 4.94 (2H,s); 4.90 (2H,s); 4.42 (2H,q, J 7 Hz); 4.06 (2H, q, j 7 Hz); 3.62 (3H,s); 2.37 (3H,s); 1.40 (3H, t, J 7 Hz); 1.17 (3H, t, J 7 Hz).

EXAMPLE 47

4-Carbamoyl-2-{[4-(2-chlorophenyl)-3-ethoxycarbonyl-5-methoxycarbonyl-6-methyl-1,4-dihydropyridin-2-yl]methoxymethyl}-thiazole A mixture of 2-{[4-(2-chlorophenyl)-3-ethoxycarbonyl-5-methoxycarbonyl-6-methyl-1,4-dihydropyridin-2-yl]methoxymethyl}-4-ethoxycarbonylthiazole (0.54 g), dioxane (20 ml) and 0.880 aqueous ammonium hydroxide solution (20 ml) was stirred at room temperature for 43 hours and then evaporated. The residue was partitioned between ethyl acetate and water and the organic layer washed with water, dried (Na₂SO₄) and evaporated. The residual oil was purified by chromatography on silica (t.l.c. grade, 10 g) using dichloromethane plus 0–3% v/v methanol as eluant. Appropriate fractions were combined and evaporated and the residual oil triturated with diethyl ether. The resulting solid was collected, washed with diethyl ether and dried to give the title compound (0.30 g) as a monohydrate, m.p. 160°–164° C. decomp.

Analysis %: Found: C, 51.27; H, 4.40; N, 7.71. $C_{23}H_{24}ClN_3O_6S.H_2O$ requires: C, 51.31; H, 4.68; N, 7.81.

EXAMPLE 48

4-Carbamoyl-2-{[4-(2,3-dichlorophenyl)-3-ethoxycarbonyl-5-methoxycarbonyl-6-methyl-1,4-dihydropyridin-2-yl]methoxymethyl}thiazole was prepared by the method of Example 47 but using 2-{[4-(2,3-dichlorophenyl)-3-ethoxycarbonyl-5-methoxycarbonyl-6-methyl-1,4-dihydropyridin-2-yl]methoxymethyl}-4-ethoxycarbonylthiazole. The product was isolated as a monohydrate and had m.p. 195°–200° C. decomp.

Analysis %: Found: C, 51.28; H, 4.40; N, 7.71. $C_{23}H_{23}Cl_2N_3O_6S.H_2O$ requires: C, 51.31; H, 4.68; N, 7.81.

EXAMPLE 49

3-Amino-5-{[4-(2-chlorophenyl)-3-ethoxycarbonyl-5-methoxycarbonyl-6-methyl-1,4-dihydropyridin-2-yl]methoxymethyl}-1,2,4-triazole A solution of 2-{[4-(2-chlorophenyl)-3-ethoxycarbonyl-5-methoxycarbonyl-6-methyl-1,4-dihydropyridin-2-yl]methoxy}-acetylhydrazine (0.87 g), 2-methylisothiourea sulphate (0.68 g) and 1,5-diazabicyclo[4.3.0]non-5-ene (0.74 g) in n-butanol (30 ml) was heated under reflux for 16 hours and then evaporated. The residue was partitioned between dichloromethane and water and the organic layer dried (Na₂SO₄) and evaporated. The residual oil was purified by chromatography on silica (t.l.c. grade, 10 g) using dichloromethane plus 0–100% v/v ethyl acetate as eluant. Appropriate fractions were combined and evaporated and the residual oil triturated with ethyl acetate. The resulting solid was collected, washed with ethyl acetate and dried to give the title compound (0.14 g), m.p. 199°–202° C. decomp.

Analysis %: Found: C, 54.77; H, 5.42; N, 14.91. $C_{21}H_{24}ClN_5O_5$ requires: C, 54.60; H, 5.24; N, 15.16.

EXAMPLE 50

1-<2-{[4-(4-Chlorophenyl)-3-ethoxycarbonyl-5-methoxycarbonyl-6-methyl-1,4-dihydropyridin-2-yl]methoxy}ethyl>-2,4,5-trimethyl-(1H)-imidazole Hexahydro-2,4,6-trimethyl-s-triazine trihydrate (0.90 g) was added portionwise over 5 minutes to a stirred, ice-cooled solution of 2-(2-aminoethoxy)methyl-4-(4-chlorophenyl)-3-ethoxycarbonyl-5-methoxycarbonyl-6-methyl-1,4-dihydropyridine (1.00 g) in methanol (10 ml) and the mixture stirred at 0° C. for one hour. A solution of diacetyl (0.84 g) in methanol (2 ml) was added dropwise over 5 minutes to the stirred, ice-cooled reaction mixture which was stirred at 0° C. for one hour and then stored overnight at −5° to 0° C. The mixture was then treated with 0.880 aqueous ammonium hydroxide solution (15 ml) and stored again overnight at −5° to 0° C. The resulting solid was collected, recrystallised from methyl isobutyl ketone and dried to give the title compound (0.55 g) as a monohydrate, m.p. 113°–115° C.

Analysis %: Found: C, 60.32; H, 6.66; N, 8.05. $C_{26}H_{32}ClN_3O_5.H_2O$ requires: C, 60.00; H, 6.54; N, 8.08.

EXAMPLE 51

5-Amino-1-<2-{[4-(2-chlorophenyl)-3-ethoxycarbonyl-5-methoxycarbonyl-6-methyl-1,4-dihydropyridin-2-yl]methoxy}ethyl>-4-ethoxycarbonylimidazole Ethyl 2-amino-2-cyanoacetate hemioxalate monohydrate (5.0 g) was partitioned between chloroform and saturated aqueous sodium bicarbonate solution and the organic layer dried ($Na_2SO_4$) and evaporated. Trimethyl orthoformate (3.80 g) was added to a solution of the resulting oil in acetonitrile (25 ml) and the mixture heated under reflux for 45 minutes and evaporated. A solution of the resulting oil in acetonitrile (10 ml) was added to a solution of 2-(2-aminoethoxy)methyl-3-ethoxycarbonyl-5-methoxycarbonyl-6-methyl-1,4-dihydropyridine (10.20 g) in acetonitrile (50 ml) and the mixture heated under reflux for 16 hours and then evaporated. The residual oil was purified by chromatography on silica (t.l.c. grade, 30 g) using dichloromethane plus 40% v/v n-hexane followed by dichloromethane plus 0-1% methanol as eluant. Appropriate fractions were combined and evaporated and the residual foam triturated with methyl isobutyl ketone. The resulting solid was collected, recrystallised from methyl isobutyl ketone and dried to give the title compound (2.80 g), m.p. 116°-118° C. This product was characterised containing 0.5 molar equivalents of methyl isobutyl ketone of solvation.

Analysis %: Found: C, 58.23; H, 6.36; N, 9.12. $C_{26}H_{31}ClN_4O_7.0.5C_6H_{12}O$ requires: C, 58.34; H, 6.20; N, 9.38.

EXAMPLE 52

2-{[4-(2,3-Dichlorophenyl)-3-ethoxycarbonyl-5-methoxycarbonyl-6-methyl-1,4-dihydropyridin-2-yl]methoxymethyl}-5-methyl-1,3,4-thiadiazole A mixture of 1-acetyl-2-{[4-(2,3-dichlorophenyl)-3ethoxycarbonyl-5-methoxycarbonyl-6-methyl-1,4-dihydropyridin-2-yl]methoxy}acetylhydrazine (1.50 g) and Lawesson's reagent (1.18 g) in acetonitrile (50 ml) was stirred at room temperature for 24 hours and then evaporated. The residue was purified by chromatography on silica (t.l.c. grade, 20 g) using dichloromethane plus 40% v/v n-hexane followed by dichloromethane plus 0-1% v/v methanol as eluant. Appropriate fractions were combined and evaporated and residual oil triturated with diethyl ether. The resulting solid was collected, washed with diethyl ether and dried to give the title compound (0.82 g), m.p. 140°-144° C.

Analysis %: Found: C, 51.42; H, 4.54; N, 7.98. $C_{22}H_{23}Cl_2N_3O_5S$ requires: C, 51.57; H, 4.52; N, 8.20.

EXAMPLE 53

2-{[4-(2,3-Dichlorophenyl)-3-ethoxycarbonyl-5-methoxycarbonyl-6-methyl-1,4-dihydropyridin-2-yl]methoxymethyl}-5-methyl-1,3,4-oxadiazole A mixture of 1-acetyl-2-{[4-(2,3-dichlorophenyl)-3-ethoxycarbonyl -5-methoxycarbonyl-6-methyl-1,4-dihydropyridin-2-yl]-methoxy }acetylhydrazine (1.33 g) and phosphorus pentoxide (1.55 g) in chloroform (70 ml) was stirred at room temperature for three days, washed thoroughly with water, dried ($MgSO_4$) and evaporated. The residue was dissolved in diethyl ether at reflux, decanted away from a small amount of insoluble oil and allowed to cool. The resulting solid was collected, recrystallised from ethyl acetate and dried to give the title compound (0.12 g), m.p. 118°-120° C.

Analysis %: Found: C, 53.02; H, 4.76; N, 8.68. $C_{22}H_{23}Cl_2N_3O_6$ requires; C,53.23; H,4.67; N,8.47.

EXAMPLE 54

5-Amino-2{[4-(2,3-dichlorophenyl)-3-ethoxycarbonyl-5-methoxycarbonyl-6-methyl-1,4-dihydropyridin-2-yl]methoxymethyl}-1,3,4-thiadiazole A solution of 1-<2-{[4-(2,3-dichlorophenyl)-3-ethoxycarbonyl-5-methoxycarbonyl-6-methyl-1,4-dihydropyridin-2-yl]methoxy}acetyl>thiosemicarbazide (1.00 g) in phosphorus oxychloride (50 ml) was stirred at room temperature for 7 hours and then evaporated. The residue was partitioned between water and chloroform and the organic layer washed with water, dried ($MgSO_4$) and evaporated. The residual oil was purified by chromatography on silica (t.l.c. grade, 5 g) using dichloromethane plus 10% v/v hexane followed by dichloromethane plus 0-5% v/v methanol as eluant. Appropriate fractions were combined and evaporated and the residual oil triturated with ethyl acetate. The resulting solid was collected, washed with ethyl acetate and dried to give the title compound (0.23 g), m.p. 194° C.

Analysis %: Found: C, 49.08; H, 4.44; N, 10.62. $C_{21}H_{22}Cl_2N_4O_5S$ requires: C, 49.13; H, 4.32; N, 10.91.

EXAMPLE 55

1-<2-{[4-(2-Chlorophenyl)-3-ethoxycarbonyl-5-methoxycarbonyl-6-methyl-1,4-dihydropyridin-2-yl]methoxy}ethyl>-2,5-dimethylpyrrole A solution of hexane-2,5-dione (0.92 g), 2-(2-aminoethoxy)methyl-4-(2-chlorophenyl)-3-ethoxycarbonyl-5-methoxycarbonyl-6-methyl-1,4-dihydropyridine (3.30 g) and acetic acid (0.10 g) in benzene (30 ml) was heated under reflux for 2 hours while the water formed was removed azeotropically, and then evaporated. The residual solid was recrystallised from cyclohexane to give the title compound (3.10 g), m.p. 103°-104° C.

Analysis %: Found: C, 64.39; H, 6.48; N, 5.74. $C_{26}H_{31}ClN_2O_5$ requires: C, 64.12; H, 6.42; N, 5.75.

EXAMPLE 56

Tablets are compounded from the following ingredients:

|  | mg/tablet |
|---|---|
| Product of any one of Examples | 10 |
| Dicalcium phosphate | 120 |
| Maize starch | 20 |
| Magnesium stearate | 1.8 |
| Sodium lauryl sulphate | 0.2 |

The ingredients are thoroughly blended, compressed, granulated and re-compressed to tablets of the desired size.

EXAMPLE 57

Capsules are compounded from the following ingredients:

|  | mg/capsule |
|---|---|
| Product of any one of Examples | 10 |
| Maize starch | 127 |
| Cellulose (microcrystalline) | 127 |

|  | mg/capsule |
| --- | --- |
| Magnesium stearate | 5.4 |
| Sodium lauryl sulphate | 0.6 |

The ingredients are thoroughly blended, then filled into hard gelatine capsules of the appropriate size to contain the ingredients.

PREPARATION 1

Ethyl 4-[2-(2,4,5-trimethyl-1-imidazolyl)ethoxy]acetoacetate 2-(2,4,5-Trimethyl-1-imidazolyl)ethanol (20 g) in dry tetrahydrofuran (150 ml) and dry dimethylformamide (5 ml) was stirred under nitrogen at room temperature while sodium hydride (50% in oil, 13.5 g) was added portionwise. The mixture was warmed briefly on a steam bath and then stirred at room temperature for one hour before adding dropwise over 5 hours a solution of ethyl 4-chloroacetoacetate (21 g) in dry tetrahydrofuran (150 ml) at room temperature. The mixture was stirred overnight, then quenched with a little ethanol and poured onto ice (120 g) and concentrated hydrochloric acid (30 ml). The tetrahydrofuran was removed by evaporation and the aqueous residue washed with petrol to remove mineral oil, basified with solid sodium carbonate and extracted with ethyl acetate (3×150 ml). The extracts were dried (Na$_2$CO$_3$), filtered and evaporated to give the ketoester as an oil (crude yield 30 g) sufficiently pure for use. N.m.r. spectrum in CDCl$_3$, $\delta$ values: 3.5–4.3 (10H, m); 2.33 (3H, s); 2.07 (6H, s); 1.23 (3H, t).

Other acetoacetate intermediates of formula (IV) wherein R$^2$ is ethyl were prepared similarly to the above, starting from the appropriate alcohol and ethyl 4-chloroacetoacetate.

PREPARATION 2

2-(2-Azidoethoxy)methyl-4-(2-chlorophenyl)-3-ethoxycarbonyl-5-methoxycarbonyl-6-methyl-1,4-dihydropyridine A solution of 2-azidoethanol (160 g) in tetrahydrofuran (300 ml) was added over 40 minutes to a suspension of sodium hydride (114 g; 80% dispersion in oil) in tetrahydrofuran (500 ml). The mixture was stirred at room temperature for 1 hour and the ice-cooled solution treated with a solution of ethyl 4-chloroacetoacetate (276 g) in tetrahydrofuran (250 ml) dropwise over 2 hours. The mixture was stirred at room temperature for 16 hours, diluted with ethanol (150 ml), and the pH adjusted to 6–7 with 4M hydrochloric acid. Sufficient water was added to dissolve the solid present and the layers were separated. The organic layer was evaporated and the residue diluted with water (600 ml) and evaporated. The residue was then partitioned between ethyl acetate and water and the aqueous layer extracted twice with ethyl acetate. The combined ethyl acetate extracts were dried (MgSO$_4$) and evaporated to give ethyl 4-(2-azidoethoxy)acetoacetate as a brown oil which was shown by g.l.c. to be 73% pure. A mixture of this crude product and ammonium acetate (92.3 g) in ethanol (600 ml) was heated under reflux for 1 hour, allowed to cool to room temperature and treated with methyl 2-(2-chlorobenzylidene)acetoacetate (286.6 g). The mixture was heated under reflux for 5.5 hours and then evaporated. The residue was stirred with methanol (1.5 l) for 16 hours and the resulting solid collected, washed twice with methanol, dried and recrystallised from methanol to give the title compound (78 g), m.p. 145°–146°.

Analysis %: Found: C, 55.39; H, 5.37; N, 13.01. C$_{20}$H$_{23}$ClN$_4$O$_5$ requires: C, 55.23; H, 5.33; N, 12.88.

PREPARATION 3

2-(2-Azidoethoxy)methyl-4-(2,3-dichlorophenyl)-3-ethoxycarbonyl-5-methoxycarbonyl-6-methyl-1,4-dihydropyridine was prepared by the method described in Preparation 2 using methyl 2-(2,3-dichlorobenzylidene)acetoacetate instead of methyl 2-(2-chlorobenzylidene)acetoacetate. The product had m.p. 141°.

Analysis %: Found: C, 55.88; H, 4.78; N, 11.73. C$_{20}$H$_{22}$Cl$_2$N$_4$O$_5$ requires: C, 51.18; H, 4.73; N, 11.94.

PREPARATION 4

2-{[4-(2-Chlorophenyl)-3-ethoxycarbonyl-5-methoxycarbonyl-6-methyl-1,4-dihydropyridin-2-yl]methoxy}acetic acid A solution of ethyl 4-(methoxycarbonylmethoxy)acetoacetate (200 g), 2-chlorobenzaldehyde (128.8 g) and methyl 3-aminocrotonate (105.4 g) in methanol (600 ml) was heated under reflux for 16 hours and then evaporated. The residue was treated with 10% aqueous sodium hydroxide solution and the mixture heated under reflux for 1.5 hours, allowed to cool to room temperature, washed three times with dichloromethane, acidified with concentrated hydrochloric acid and extracted into dichloromethane. The dichloromethane extracts were washed with water, dried over magnesium sulphate and evaporated. The residue was recrystallised from ethyl acetate to give the title compound (63 g), m.p. 150°–154° C.

Analysis %: Found: C, 56.63; H, 5.24; N, 3.39. C$_{20}$H$_{22}$ClNO$_7$ requires: C, 56.67; H, 5.23; N, 3.30.

PREPARATION 5

2-{[4-(2,3-Dichlorophenyl)-3-ethoxycarbonyl-5-methoxycarbonyl-6-methyl-1,4-dihydropyridin-2-yl]methoxy}acetic acid was prepared by the method of Preparation 4 but using 2,3-dichlorobenzaldehyde as starting material. The product had m.p. 160°–162° C.

Analysis %: Found: C, 52.32; H, 4.60; N, 3.05. C$_{20}$H$_{21}$Cl$_2$NO$_7$ requires: C, 52.41; H, 4.62; N, 3.06.

PREPARATION 6

2-{[4-(2-Chlorophenyl)-3-ethoxycarbonyl-5-methoxycarbonyl-6-methyl-1,4-dihydropyridin-2-yl]methoxy}acetamide Carbonyldiimidazole (9.80 g) was added to a suspension of 2-{[4-(2-chlorophenyl)-3-ethoxycarbonyl-5-methoxycarbonyl-6-methyl-1,4-dihydropyridin-2-yl]methoxy}acetic acid (25.4 g) in tetrahydrofuran (400 ml) and the mixture stirred at room temperature for 2 hours. A stream of gaseous ammonia was passed through the resulting solution with stirring until the reaction was complete (as determined by t.l.c.) The reaction mixture was evaporated and the residue partitioned between ethyl acetate and water. The organic layer was washed with water, dried over sodium sulphate and evaported. The residue was triturated with diethyl ether and the resulting solid collected, recrystallised from diethyl ether/n-hexane and dried to give the title compound (17.0 g), m.p. 127°–128° C.

Analysis %: Found: C, 56.70; H, 5.42; N, 6.60. C_{20}H_{23}ClN_{2}O_{6} requires: C, 56.60; H, 5.48; N, 6.63.

PREPARATIONS 7-10

The following compounds were prepared by the method described in Preparation 6 using the appropriate amine starting materials.

| Preparation No. | R | R$^5$ | m.p. (°C.) | Analysis % (Theoretical in brackets) C | H | N |
|---|---|---|---|---|---|---|
| 7 | 2,6-diCl-C$_6$H$_3$ | NH$_2$ | 55–60 | 52.86 (52.53 | 5.11 4.85 | 7.27 6.13) |
| 8 | 2,6-diCl-C$_6$H$_3$ | NHNH.CNH$_2$ (C=S) | 95–100 | Characterised by N.m.r. spectra | | |
| 9 | 2,6-diCl-C$_6$H$_3$ | NHNH.CCH$_3$ (C=O) | Oil | Characterised by N.m.r. spectra | | |
| 10 | 2-Cl-C$_6$H$_4$ | NHNH$_2$ | 134–136 | 54.57 (54.86 | 5.62 5.52 | 9.54 9.60) |

PREPARATION 11

2-{[4-(2-Chlorophenyl)-3-ethoxycarbonyl-5-methoxycarbonyl-6-methyl-1,4-dihydropyridin-2-yl]methoxy}acetonitrile A solution of trifluoroacetic anhydride (0.56 g) in dioxane (5 ml) was added dropwise over 5 minutes to a stirred, ice-cooled solution of 2-{[4-(2-chlorophenyl)-3-ethoxycarbonyl-5-methoxycarbonyl-6-methyl-1,4-dihydropyridin-2-yl]methoxy}acetamide (0.84 g) and pyridine (0.32 g) in dioxane (25 ml). The mixture was stirred at room temperature for 4 hours, diluted with water and extracted into ethyl acetate. The ethyl acetate extract was washed with water, dried over sodium sulphate and evaporated. The residue was purified by chromatography on silica (10 g) eluting with dichloromethane plus 0–2% v/v methanol. Appropriate fractions were combined and evaporated to give the total compound (0.60 g), m.p 128°–130° C.

Analysis %: Found: C, 59.63; H, 5.26; N, 7.11. C_{20}H_{21}ClN_{2}O_{5} requires: C, 59.33; H, 5.23; N, 6.92.

PREPARATION 12

2-{[4-(2,3-Dichlorophenyl)-3-ethoxycarbonyl-5-methoxycarbonyl-6-methyl-1,4-dihydropyridin-2-yl]methoxy}acetonitrile was prepared by the method of Preparation 11 but starting with 2-{[4-(2,3-dichlorophenyl)-3-ethoxycarbonyl-5-methoxycarbonyl-6-methyl-1,4-dihydropyridin-2-yl]methoxy}acetamide. The product had m.p. 117°–118° C.

Analysis %: Found: C, 54.60; H, 4.52; N, 6.36. C_{20}H_{20}Cl_{2}N_{2}O_{5} requires: C, 54.68; H, 4.59; N, 6.38.

PREPARATION 13

2-{[4-(2-Chlorophenyl)-3-ethoxycarbonyl-5-methoxycarbonyl-6-methyl-1,4-dihydropyridin-2-yl]methoxy}thioacetamide A mixture of 2-{[4-(2-chlorophenyl)-3-ethoxycarbonyl-5-methoxycarbonyl-6-methyl-1,4-dihydropyridin-2-yl]methoxy}-acetamide (6.8 g) and Lawesson's reagent (6.4 g) in acetonitrile (300 ml) was stirred at room temperature for 2.5 hours, filtered and evaporated. The residue was purified by chromatography on silica (80 g) using dichloromethane plus 0–10% v/v ethyl acetate as eluant. Appropriate fractions were combined and evaporated and the residual oil triturated with diethyl ether. The resulting solid was collected, washed with diethyl ether and dried to give the title compound (5.9 g), m.p. 149°–150° C.

Analysis %: Found: C, 54.38; H, 5.29; N, 6.37. C_{20}H_{23}ClN_{2}O_{5}S requires: C, 54.74; H, 5.28; N, 6.38.

PREPARATION 14

2-{[4-(2,3-Dichlorophenyl)-3-ethoxycarbonyl-5-methoxycarbonyl-6-methyl-1,4-dihydropyridin-2-yl]methoxy}thioacetamide was prepared by the method of Preparation 13 but using 2-{[4-(2,3-dichlorophenyl)-3-ethoxycarbonyl-5-methoxycarbonyl-6-methyl-1,4-dihydropyridin-2-yl]methoxy}acetamide as starting material. The product had m.p. 185°–187° C. decomp.

Analysis %: Found: C, 50.73; H, 4.61; N, 5.78. C_{20}H_{22}Cl_{2}N_{2}O_{5}S requires: C, 50.75; H, 4.69; N, 5.92.

PREPARATION 15

Ethyl 4-(methoxycarbonylmethoxy)acetoacetate

Methyl 2-(chloroformylmethoxy)acetate (216.6 g) was added over 45 minutes to a stirred solution of 2,2-dimethyl-1,3-dioxane-4,6-dione (173.9 g) and pyridine (189.6 g) in dichloromethane (1000 ml) keeping the temperature below 5° C. The mixture was stirred at 5° C. for 30 minutes, allowing to warm up to room temperature over one hour, washed with 2.4M hydrochloric acid and water, dried over magnesium sulphate and evaporated. The resulting browm oil was dissolved in ethanol (300 ml) and the solution heated under reflux for 2.5 hours and evaporated. The residual oil was distilled to give the title compound (32.5 g), b.p. 138°–140°/1 torr which was characterised by its N.m.r. spectrum in CDCl$_3$, δ values: 4.27 (2H,s); 4.20 (2H, q, J 7 Hz); 4.16 (2H,s); 3.75 (3H, s); 3.54 (2H, s); 1.29 (3H, t, J 7 Hz).

We claim:

1. A 1,4-dihydropyridine compound having the formula:

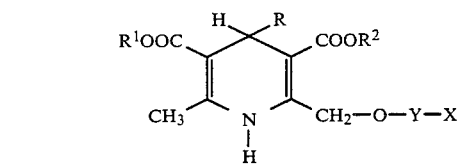

or a pharmaceutically acceptable addition salt thereof wherein:

R is 2-chlorophenyl or 2,3-dichlorophenyl;

$R^1$ and $R^2$ are each independently $C_1$-$C_4$ alkyl or 2-methoxyethyl;

Y is —$(CH_2)_n$—, —$CH_2CH(CH_3)$— or —$CH_2C(CH_3)_2$—;

n is an integer from 1 to 3; and

X is a triazolyl ring or said ring substituted by cyano, carboxy, carbamoyl, amino or $CO_2(C_1$-$C_4$ alkyl) groups with the proviso that if the triazolyl ring is linked to Y by a ring nitrogen atom n is 2 or 3.

2. A compound according to claim 1 wherein X is 1,2,3-(1H)-triazol-1-yl, 4-carbamoyl-1,2,3-(1H)-triazol-1-yl or 3-amino-1,2,4-triazol-5-yl.

3. A compound according to claim 2 wherein $R^1$ and $R^2$ are methyl or ethyl.

4. A compound according to claim 1 which is 4-(2-([4-(2,3-dichlorophenyl)-3-ethoxycarbonyl-5-methoxycarbonyl-6-methyl-1,4-dihydropyridin-2-yl]-methoxy)ethyl)-1,2,4-(4H)-triazole.

5. A pharmaceutical composition comprising an effective amount of an antihypertensive compound according to claim 1 and a pharmaceutically acceptable diluent or carrier.

6. A method of treating or preventing hypertension in man comprising administering an antihypertensive effective amount of a compound according to claim 1.

* * * * *